United States Patent [19]

Krapcho et al.

[11] 3,983,106

[45] *Sept. 28, 1976

[54] 5-HETEROCYCLICALKYL-2-ARYL-3-HALO 1,5-BENZOTHIAZEPIN-4(5H)-ONES

[75] Inventors: John Krapcho, Somerset; Chester F. Turk, Kendall Park, both of N.J.

[73] Assignee: E. R. Squibb & Sons, Inc., Princeton, N.J.

[ * ] Notice: The portion of the term of this patent subsequent to July 15, 1992, has been disclaimed.

[22] Filed: July 3, 1975

[21] Appl. No.: 592,966

[52] U.S. Cl. .................... 260/239.3 B; 424/244; 424/250; 424/267; 424/248; 424/274; 424/273; 424/272
[51] Int. Cl.² .................................... C07D 281/02
[58] Field of Search .................... 260/239.3 B

[56] References Cited
UNITED STATES PATENTS

| | | | |
|---|---|---|---|
| 3,075,967 | 1/1963 | Krapcho | 260/239.3 B |
| 3,075,968 | 1/1963 | Krapcho | 260/239.3 B |
| 3,155,649 | 11/1964 | Krapcho et al. | 260/239.3 B |
| 3,562,257 | 2/1971 | Kugita et al. | 260/239.3 B |
| 3,646,008 | 2/1972 | Kugita et al. | 260/239.3 B |
| 3,895,006 | 7/1975 | Krapcho et al. | 260/239.3 B |

*Primary Examiner*—Henry R. Jiles
*Assistant Examiner*—Robert T. Bond
*Attorney, Agent, or Firm*—Lawrence S. Levinson; Merle J. Smith; Donald J. Barrack

[57] ABSTRACT

Novel benzothiazepines having the structure

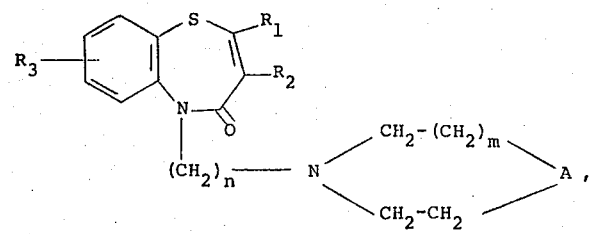

the pharmaceutically acceptable salts thereof, the quaternary ammonium salts thereof, and the 1-oxide and 1,1-dioxide derivatives thereof; wherein $R_1$ is phenyl or substituted phenyl; $R_2$ is chlorine or bromine; $R_3$ is hydrogen, alkyl, alkoxy, halogen, or trifluoromethyl; $n$ is 2, 3, or 4; $m$ is 0, 1 or 2, A is CH—$R_4$, N—$R_5$ or oxygen, $R_4$ is hydrogen or alkyl, and $R_5$ is hydrogen, alkyl, monohydroxyalkyl, phenyl, or substituted phenyl, provided that when $m$ is 0 or 2, A is CH—$R_4$; have useful pharmacological activity.

10 Claims, No Drawings

5-HETEROCYCLICALKYL-2-ARYL-3-HALO 1,5-BENZOTHIAZEPIN-4(5H)-ONES

SUMMARY OF THE INVENTION

Compounds having the structure

I 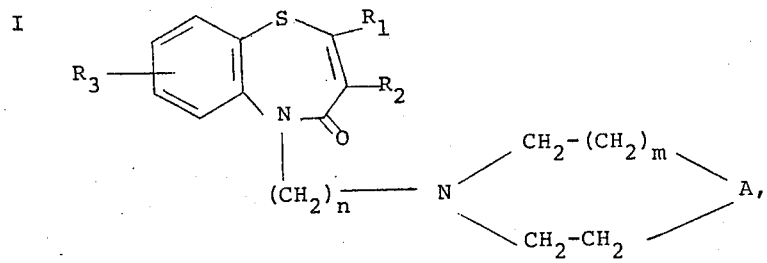

the pharmaceutically acceptable salts thereof, the quaternary ammonium salts thereof, and the 1-oxide and 1,1-dioxide derivatives thereof, have useful anti-inflammatory activity. In formula I, and throughout the specification, the symbols are as defined below.

$R_1$ can be phenyl or phenyl monosubstituted with alkyl, alkoxy, halogen, trifluoromethyl or

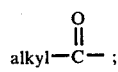

$R_2$ can be chlorine or bromine;
$R_3$ can be hydrogen, alkyl, alkoxy, halogen, or trifluoromethyl;
$n$ can be 2, 3, or 4; and
$m$ can be 0, 1 or 2, A can be CH—$R_4$, N—$R_5$ or oxygen, $R_4$ can be hydrogen or alkyl, and $R_5$ can be hydrogen, alkyl, monohydroxyalkyl, phenyl or phenyl monosubstituted with alkyl, alkoxy, halogen, trifluoromethyl or

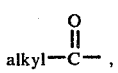

provided that when $m$ is 0 or 2, A is CH—$R_4$.

The term "alkyl" as used throughout the specification refers to straight and branched chain alkyl groups having 1 to 6 carbon atoms, e.g., methyl, ethyl, propyl, isopropyl, butyl, t-butyl, pentyl, hexyl, and the like. Alkyl groups having 1 to 3 carbon atoms are preferred.

The term "alkoxy" as used throughout the specification refers to groups having the formula alkyl-O-, wherein alkyl is as defined above.

The term "halogen" as used throughout the specification refers to fluorine, chlorine, bromine, and iodine; chlorine and bromine are the preferred halogens.

Exemplary of the heterocyclic moieties contemplated by the formula

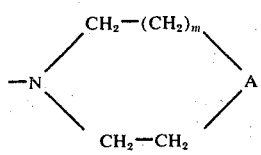

are 1-pyrrolidinyl, 1-piperidinyl, 4-morpholinyl, 1-piperazinyl, 1-homopiperidinyl, 4-alkyl-1-piperazinyl, 4-alkyl-1-piperidinyl, 3-alkyl-1-pyrrolidinyl, 4-alkyl-1-homopiperidinyl, 4-hydroxyalkyl-1-piperazinyl, 4-phenyl-1-piperazinyl, and 4-substituted phenyl-1-piperazinyl.

DETAILED DESCRIPTION OF THE INVENTION

The compounds of this invention are prepared using as starting materials 2,3-dihydro-2-aryl-1,5-benzothiazepine-4(5H)-ones having the structure II 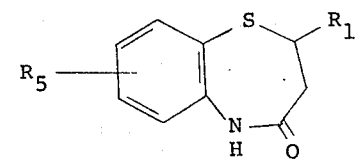

The starting materials of formula II are known; see, for example, U.S. Pat. No. 3,075,967.

A chlorine or bromine atom can be introduced into the 3-position of a benzothiazepine of formula II by reaction of the benzothiazepine with N-chloro or N-bromosuccinimide. The reaction can be run in an organic solvent, preferably a polar organic solvent such as dimethylformamide. Reaction conditions are not critical, but the reaction should be run at an elevated temperature of from about 70°C to 110°C for about 1 hour to 8 hours. The resulting 3-halo-2-aryl-1,5-benzothiazepin-4(5H)-ones have the structure III 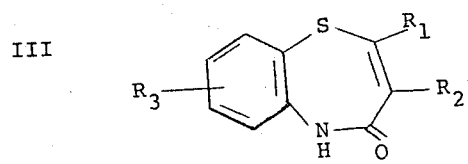

Compounds of formula I can be prepared by reacting the appropriate 3-halo-2-aryl-1,5-benzothiazepin-4(5H)-one of formula III with a salt having the structure

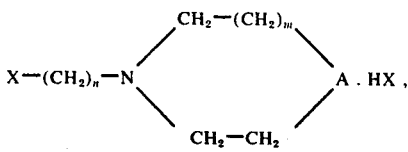

wherein X is chlorine or bromine. The reaction can be carried out in an organic solvent, e.g., benzene, toluene, xylene, etc., in the presence of a strong base, e.g. sodium hydroxide, sodium hydride or the like. Reaction conditions are not critical, and the reaction will usually be carried out with heating.

In some instances it is advantageous to introduce the basic side chain onto a compound of formula III by a two-step procedure. A compound of formula III is first reacted with a compound having the structure

to yield an intermediate having the structure

VI

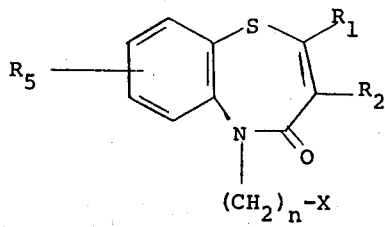

Reaction of an intermediate of formula VI with a compound having the formula

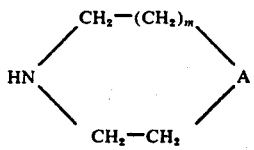

yields the compounds of formula I. The reaction can be run in an inert solvent such as toluene, at an elevated temperature. Optionally, a catalyst such as sodium iodide can be present.

Compounds of formula I wherein $n$ is 2 or 3 are preferred.

The compounds of formula I form acid addition salts with inorganic and organic acids. These acid addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide which are preferred, sulfate, nitrate, phosphate, borate, acetate, tartrate, maleate, citrate, succinate, benzoate, ascorbate, salicylate, methanesulfonate, benzenesulfonate, toluenesulfonate and the like.

The 1-oxide and 1,1-dioxide derivatives of the compounds of formula I can be prepared using techniques well known in the art. Oxidation of a compound of formula I using hydrogen peroxide yields the corresponding sulfoxide derivative. Oxidation of a compound of formula I using potassium permanganate yields the corresponding sulfonyl derivative. Alternatively, the sulfoxide and sulfonyl derivatives can be prepared by treating compounds of formula I with m-chloroperbenzoic acid. Treating a compound of formula I with an equivalent of m-chloroperbenzoic acid for from 2 to 24 hours at room temperature yields the corresponding sulfoxide derivative. Treating a compound of formula I, or a sulfoxide derivative of a compound of formula I, with two equivalents of m-chloroperbenzoic acid for 2 to 24 hours at room temperature (or for a shorter time with slight heating) yields the corresponding sulfonyl derivative.

The compounds of formula I form quaternary ammonium salts with alkyl halides (e.g., methyl chloride, isobutyl bromide, dodecyl chloride and cetyl iodide), benzyl halides (e.g., benzyl chloride, and dialkyl sulfates (e.g., dimethyl sulfate).

The compounds of formula I, the pharmaceutically acceptable salts thereof, the quaternary ammonium salts thereof, and the 1-oxide and 1,1-dioxide derivatives thereof, are useful for the treatment of inflammation in mammalian species, e.g., rats, dogs, cats, monkeys, etc. Joint tenderness and stiffness (in conditions such as rheumatoid arthritis) can be relieved by the above described compounds.

The compounds of this invention are formulated for use as anti-inflammatory agents according to accepted pharmaceutical practice in oral dosage forms such as tablets, capsules, elixirs or powders, or in an injectable form in a sterile aqueous vehicle prepared according to conventional pharmaceutical practice. The compounds of this invention can be administered in amounts of 100 milligrams per kilogram of animal body weight per day to 2 grams per kilogram of animal body weight per day, preferably 100 milligrams per kilogram of animal body weight per day to 1 gram per kilogram of animal body weight per day.

The following examples are specific embodiments of this invention.

EXAMPLE 1

3-Chloro-5-[3-(4-methyl-1-piperazinyl)propyl]-2-phenyl-1,5-benzothiazepin-4(5$\underline{H}$)-one, hydrochloride (1:2)

A. 3-Chloro-2-phenyl-1,5-benzothiazepin-4(5$\underline{H}$)-one 2,3-Dihydro-2-phenyl-1,5-benzothiazepin-4(5$\underline{H}$)-one (25.5 grams, 0.1 mole) is stirred in 250 ml of dimethylformamide. To the stirred solution is added a solution of N-chlorosuccinimide (27 grams, 0.2 mole) in 100 ml of dimethylformamide. The mixture is stirred at 105°–110°C for 5 hours, followed by cooling. The cooled solution is poured into 1.8 liters of cold water and a solid precipitates. The crude product (28 grams) has a melting point of 238°–240°C. The crude product is crystallized from a mixture of 30 ml hot dimethylformamide and 90 ml acetonitrile yielding 26.2 grams of the title compound, melting point 241°–243°C.

B. 3-Chloro-5-[3-(4-methyl-1-piperazinyl)propyl]-2-phenyl-1,5-benzothiazepin-4(5$\underline{H}$)-one, hydrochloride (1:2)

3-Chloro-2-phenyl-1,5-benzothiazepin-4(5H)-one (6.5g) is reacted in 125 ml of toluene with 3.7g of propyl)-4-methylpiperazine.2HBr, the compound listed in column III is obtained.

| Example | Column I | Column II | Column III |
|---|---|---|---|
| 2 | 2,3-dihydro-7-methyl-2-phenyl-1,5-benzothiazepin-4(5H)-one | 1-(2-bromoethyl)piperazine.2HBr | 3-chloro-7-methyl-2-phenyl-5-[2-(1-piperazinyl)ethyl]-1,5-benzothiazepin-4(5H)-one, hydrochloride |
| 3 | 7-ethoxy-2,3-dihydro-2-phenyl-1,5-benzothiazepin-4(5H)-one | 1-(3-bromopropyl)piperidine.HBr | 3-chloro-7-ethoxy-2-phenyl-5-[3-(1-piperidyl)propyl]-1,5-benzothiazepin-4(5H)-one, hydrochloride |
| 4 | 7-chloro-2,3-dihydro-2-phenyl-1,5-benzothiazepin-4(5H)-one | 1-(4-bromobutyl)-4-methylpiperidine.HBr | 3,7-dichloro-5-[4-(4-methyl-1-piperidyl)butyl]-2-phenyl-1,5-benzothiazepin-4(5H)-one, hydrochloride |
| 5 | 2,3-dihydro-2-phenyl-7-(trifluoromethyl)1,5-benzothiazepin-4(5H)-one | 1-(3-bromopropyl) pyrrolidine.HBr | 3-chloro-2-phenyl-5-[3-(1-pyrrolidinyl)propyl]-7-(trifluoromethyl)-1,5-benzothiazepin-4(5H)-one, hydrochloride |
| 6 | 2,3-dihydro-7-methyl-2-phenyl-1,5-benzothiazepin-4(5H)-one | 1-(2-bromoethyl)-3-methylpyrrolidine.HBr | 3-chloro-7-methyl-5-[2-(3-methyl-1-pyrrolidinyl)ethyl]-2-phenyl-1,5-benzothiazepin-4(5H)-one, hydrochloride |
| 7 | 2,3-dihydro-2-(p-methoxyphenyl)-1,5-benzothiazepin-4(5H)-one | 1-(2-bromoethyl)-4-methylpiperazine.2HBr | 3-chloro-2-(p-methoxyphenyl)-5-[2-(4-methyl-1-piperazinyl)ethyl]-1,5-benzothiazepin-4(5H)-one, hydrochloride |
| 8 | 2-(p-chlorophenyl)-2,3-dihydro-1,5-benzothiazepin-4(5H)-one | 1-(4-bromobutyl)piperazine.2HBr | 3-chloro-2-(p-chlorophenyl)-5-[4-(1-piperazinyl)butyl]-1,5-benzothiazepin-4(5H)-one, hydrochloride |
| 9 | 2,3-dihydro-2-(p-isopropylphenyl)-1,5-benzothiazepin-4(5H)-one | 1-(3-bromopropyl)piperazine.2HBr | 3-chloro-2-(p-isopropylphenyl)-5-[3-(1-piperazinyl)propyl]-1,5-benzothiazepin-4(5H)-one, hydrochloride |
| 10 | 2,3-dihydro-2-[p-(trifluoromethyl)phenyl]-1,5-benzothiazepin-4(5H)-one | 4-(3-bromopropyl)morpholine.HBr | 3-chloro-5-[3-(4-morpholinyl)propyl]-2-[p-(trifluoromethyl)phenyl]-1,5-benzothiazepin-4(5H)-one, hydrochloride |
| 11 | 2-(p-acetylphenyl)-2,3-dihydro-1,5-benzothiazepin-4(5H)-one | 4-(2-bromoethyl)morpholine.HBr | 2-(p-acetylphenyl)-3-chloro-5-[2-(4-morpholinyl)ethyl]-1,5-benzothiazepin-4(5H)-one, hydrochloride |
| 12 | 2,3-dihydro-2-phenyl-1,5-benzothiazepin-4(5H)-one | 1-(2-bromoethyl)homopiperidine.HBr | 3-chloro-5-[2-(1-homopiperidinyl)ethyl]-2-phenyl-1,5-benzothiazepin-4(5H)-one, hydrochloride |
| 13 | 2,3-dihydro-2-phenyl-1,5-benzothiazepin-4(5H)-one | 1-(3-bromopropyl)-4-methylhomopiperidine.HBr | 3-chloro-5-[3-(4-methyl-1-homopiperidinyl)propyl]-2-phenyl-1,5-benzothiazepin-4(5H)-one, hydrochloride | powdered sodium hydroxide and 12g of 1-(3-bromopropyl)-4-methylpiperazine.2-HBr. This suspension is stirred and heated on a steam bath for 30 minutes, cooled and treated with 50 ml of water. The organic phase is separated, shaken with a cold solution of 8 ml of concentrated hydrochloric acid in 100 ml of water and the layers are separated. The aqueous phase is cooled, layered over with 100 ml of ether, stirred, and made alkaline by the addition of 16g of potassium carbonate. The layers are separated, the aqueous phase is extracted with three 150 ml portions of ether, the combined organic layers are dried over magnesium sulfate, and the solvent is removed on a rotary evaporator to give 8.0g of a glass-like base. The base is dissolved in 150 ml of chloroform, cooled, treated with 6.5 ml of 7.1 N ethanolic hydrogen chloride, and the solvents evaporated. The residue (11.5g) is triturated with 100 ml of warm acetonitrile and ether to give a solid which is dried in vacuo and recrystallized from a mixture of 80 ml of methanol and 100 ml of ether to give 7.3g of the title compound, melting point 239°–241°C, with dec.

EXAMPLES 2–12

Following the procedure of Example 1, but substituting the compound listed in column I below for 2,3-dihydro-2-phenyl-1,5-benzothiazepin-4(5H)-one and the compound listed in column II below for 1-(3-bromo-

EXAMPLE 14

3-Chloro-5-[3-(4-methyl-1-piperazinyl)propyl]-2-phenyl-1,5-benzothiazepin-4(5H)-one-1-oxide, dihydrochloride 3-Chloro-5-[3-(4-methyl-1-piperazinyl)propyl]-2-phenyl-1,5-benzothiazepin-4(5H)-one, hydrochloride (prepared as described in Example 1) is treated with one equivalent of hydrogen peroxide in dilute acetic acid, and allowed to stand for about 16 hours. Solvent removal yields the title compound.

EXAMPLE 15

3-Chloro-5-[3-(4-methyl-1-piperazinyl)propyl]-2-phenyl-1,5-benzothiazepin-4(5H)-one-1,1-dioxide, hydrochloride, hydrate 3-Chloro-5-[3-(4-methyl-1-piperazinyl)propyl]-2-phenyl-1,5-benzothiazepin-4(5H)-one, hydrochloride, (prepared as described in Example 1) is refluxed with two equivalents of a chloroform solution of m-chloroperbenzoic acid to yield the title compound.

EXAMPLE 16

3-Bromo-5-[3-(4-methyl-1-piperazinyl)propyl]-2-phenyl-1,5-benzothiazepin-4(5H)-one, hydrochloride (1:2)

Following the procedure of Example 1, but substituting N-bromosuccinimide for N-chlorosuccinimide, yields the title compound.

EXAMPLE 17

3-Chloro-5-[3-[4-(2-hydroxyethyl)-1-piperazinyl]propyl]-2-phenyl-1,5-benzothiazepin-4(5H)-one, hydrochloride (1:2)

A mixture of 6.5g of 3-chloro-2-phenyl-1,5-benzothiazepin-4(5H)-one (prepared as described in Example 1A) in 125 ml of toluene is treated with 1.2g of 50% sodium hydride dispersion and stirred for 1 hour at room temperature. The mixture is then treated with 3.6g of 1-bromo-3-chloropropane and refluxed for 2 hours. After cooling, the mixture is extracted with two 50 ml portions of water and the organic phase is dried over magnesium sulfate, filtered and the filtrate is treated with 9.0g of N-(2-hydroxyethyl)piperazine and 1g of potassium iodide. This mixture is stirred, refluxed for 8 hours, cooled and extracted with two 50 ml portions of water. The organic phase is dried over magnesium sulfate, filtered and the filtrate treated with two equivalents of ethanolic hydrogen chloride to yield the title compound.

EXAMPLES 18-23

Following the procedure of Example 17, but substituting the compound listed in column I for N-(2-hydroxyethyl)piperazine, the compound listed in column II is obtained.

What is claimed is:

1. A compound having the formula

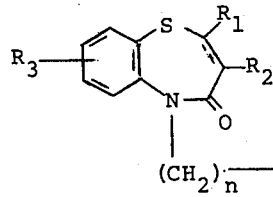
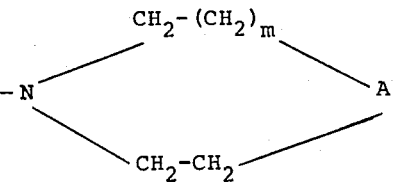

or a pharmaceutically acceptable salt thereof, or a quaternary ammonium salt thereof formed with an alkyl halide, a benzyl halide, or a dialkyl sulfate, or a 1-oxide or 1,1-dioxide derivative thereof; wherein $R_1$ is phenyl or substituted phenyl; $R_2$ is chlorine or bromine; $R_3$ is hydrogen, alkyl, alkoxy, halogen, or trifluoromethyl; $n$ is 2, 3, or 4; and $m$ is 0, 1 or 2, A is CH-$R_4$, N-$R_5$ or oxygen, $R_4$ is hydrogen or alkyl, and $R_5$ is hydrogen, alkyl, monohydroxyalkyl, phenyl or substituted phenyl, provided that when $m$ is 0 or 2, A is CH-$R_4$; and wherein substituted phenyl refers to phenyl monosubstituted with alkyl, alkoxy, halogen or trifluoromethyl, and alkyl and alkoxy, whether used alone or as part of another term, in each and all instances employed, refer to groups having 1 to 6 carbon atoms.

2. A compound in accordance with claim 1 wherein $R_1$ is phenyl.

3. A compound in accordance with claim 1 wherein $R_2$ is chlorine.

4. A compound in accordance with claim 1 wherein $R_2$ is bromo.

5. A compound in accordance with claim 1 wherein $n$ is 2 or 3.

6. A compound in accordance with claim 1 wherein $n$ is 2.

| | Column I | Column II |
|---|---|---|
| 18 | N-phenylpiperazine | 3-chloro-5-[3-(4-phenyl-1-piperazinyl)propyl]-2-phenyl-1,5-benzothiazepin-4(5H)-one, hydrochloride |
| 19 | N-(3-methylphenyl)piperazine | 3-chloro-5-[3-[4-(3-methylphenyl)-1-piperazinyl]propyl]-2-phenyl-1,5-benzothiazepin-4(5H)-one, hydrochloride |
| 20 | N-(3-methoxyphenyl)piperazine | 3-chloro-5-[3-[4-(3-methoxyphenyl)-1-piperazinyl]propyl]-2-phenyl-1,5-benozthiazepin-4(5H)-one, hydrochloride |
| 21 | N-(2-chlorophenyl)piperazine | 3-chloro-5-[3-[4-(2-chlorophenyl)-1-piperazinyl]propyl]-2-phenyl-1,5-benzothiazepin-4(5H)-one, hydrochloride |
| 22 | N-(4-trifluoromethylphenyl)piperazine | 3-chloro-5-[3-[4-(4-trifluoromethylphenyl)-1-piperazinyl]propyl]-2-phenyl-1,5-benzothiazepin-4(5H)-one, hydrochloride |
| 23 | N-(4-acetylphenyl)piperazine | 3-chloro-5-[3-[4-(4-acetylphenyl)-1-piperazinyl]propyl]-2-phenyl-1,5-benzothiazepin-4(5H)-one, hydrochloride |

7. A compound in accordance with claim 1 wherein $n$ is 3.

8. A compound in accordance with claim 1 wherein $m$ is 1 and A is N-$R_5$.

9. A compound in accordance with claim 8 wherein $R_5$ is hydrogen or alkyl.

10. The compound in accordance with claim 9 having the name 3-chloro-5-[3-(4-methyl-1-piperazinyl)-propyl]-2-phenyl-1,5-benzothiazepin-4(5$\underline{H}$)-one, hydrochloride (1:2).

* * * * *